United States Patent [19]
Kim et al.

[11] Patent Number: 5,972,293
[45] Date of Patent: Oct. 26, 1999

[54] AQUEOUS COMPOSITIONS FOR MAKING ULTRAPURE WATER USED IN MICROELECTRONIC DEVICE FABRICATION PROCESSES AND METHODS OF STERILIZING ULTRAPURE WATER DELIVERY SYSTEMS USING THE SAME

[75] Inventors: Seung-uhn Kim; Yun-chul Oh; Sue-ryeon Kim; Jung-sung Hwang, all of Kyungki-do, Rep. of Korea

[73] Assignee: Samsung Electronics Co., Ltd., Kyungki-do, Rep. of Korea

[21] Appl. No.: 09/061,990

[22] Filed: Apr. 17, 1998

[30] Foreign Application Priority Data

Apr. 22, 1997 [KR] Rep. of Korea ............ 97-14955

[51] Int. Cl.$^6$ ........................................... A61L 2/18
[52] U.S. Cl. ............................. 422/28; 210/900
[58] Field of Search .................. 422/24, 28, 7, 422/14, 17, 292; 210/900; 134/902; 424/62, 405, 616; 514/714, 557

[56] References Cited

U.S. PATENT DOCUMENTS

| | | |
|---|---|---|
| 5,024,766 | 6/1991 | Mahmud . |
| 5,160,429 | 11/1992 | Ohmi et al. . |
| 5,259,972 | 11/1993 | Miyamuru et al. ........... 210/652 |
| 5,279,735 | 1/1994 | Cosentino et al. . |
| 5,731,275 | 3/1998 | Prevost et al. . |

*Primary Examiner*—Elizabeth McKane
*Attorney, Agent, or Firm*—Myers Bigel Sibley & Sajovec

[57] ABSTRACT

Compositions for making ultrapure water in microelectronic device fabrication processes comprise hydrogen peroxide, peracetic acid, and water. Methods of sterilizing ultrapure water delivery systems for use in microelectronic device fabrication processes comprise contacting ultrapure water delivery systems with water having temperatures ranging from about 26° C. to about 40° C.; and sterilizing the ultrapure water delivery systems with compositions comprising hydrogen peroxide, peracetic acid, and water. The ultrapure water delivery systems comprise water tanks, heat exchangers in fluid communication with the water tanks, ultraviolet sterilizers in fluid communication with the heat exchangers, OR-polishers in fluid communication with the ultraviolet sterilizers, MB-polishers in fluid communication with the OR-polishers, and ultrafilters in fluid communication with the OR-polishers. The compositions employed in the sterilizing step do not contact the OR-polishers and the MB-polishers.

10 Claims, 3 Drawing Sheets

AQUEOUS COMPOSITIONS FOR MAKING ULTRAPURE WATER USED IN MICROELECTRONIC DEVICE FABRICATION PROCESSES AND METHODS OF STERILIZING ULTRAPURE WATER DELIVERY SYSTEMS USING THE SAME

FIELD OF THE INVENTION

The invention generally relates to compositions used in conjunction with microelectronic device fabrication and methods of employing the compositions.

BACKGROUND OF THE INVENTION

In microelectronic (e.g., semiconductor) device fabrication processes, it is highly desirable to use water having a high purity level, e.g., ultrapure water, which typically contains little or no microorganisms. It is typically important to use highly purified water since long contact times are often required by the wafers being treated with the water during fabrication. Unless the water is highly purified, it may serve as a source of wafer contamination since the water often contains impurities such as water-soluble minerals and particulate matter. Additionally, it may be desirable to introduce the ultrapure water to fabrication processing sites via a line which is isolated from potential sources of contamination.

Conventional methods of obtaining ultrapure water have typically focused on techniques relating to sieve filtering, reverse osmosis, active carbon layer filtering, degassing, and ion-adsorption via ion exchange for removing water-soluble minerals and particulates. Moreover, ultraviolet radiation has been used in an attempt to remove microorganisms such as bacteria from the water.

Difficulties in obtaining ultrapurified water have been experienced with respect to the removal of microorganisms. In particular, it is often difficult to completely remove the microorganisms from the water. Moreover, since microorganisms are usually present in the atmosphere, treated water can be recontaminated. Contamination attributable to microorganisms may be exacerbated by the formation of a biofilm which results in biofouling. As known in the art, biofilm is typically defined as a gel-like substance formed by the interaction of microorganisms and extracellular polymeric materials (EPS). These materials typically grow on a substratum solid-liquid interface in an aqueous environment. A biofilm composition may comprise 70 to 95 percent by weight of water. Typically, between 70 to 95 weight percent of dry materials which are present in the biofilm are organic materials. Microorganisms are usually present inside of the biofilm. The chemical structure of a biofilm can vary according to various factors such as, for example, the specific types of microorganisms present in the biofilm and the environmental conditions of the biofilm. A common chemical structure present in the biofilm is polysaccharide, and a biofilm containing this material is known as glycocalyx.

A biofilm may be spread uniformly over the entire surface of a piece of processing equipment, or it may spread in an intermittent fashion. The biofilm is usually thin with a maximum thickness being in the hundreds of microns. Since biofilm can prevent the diffusion of dissolved oxygen, anaerobic microorganisms may be contained in a biofilm as thin as about 50 to 150 $\mu$m.

A biofilm is usually heterogeneous in structure due to the various kinds of microorganisms present therein and due to the ever-changing types of microorganisms present in the biofilm. Nonetheless, the biofilm often exhibits functional homogeneity since the microorganisms typically exist in the form of microconsortia which usually function in a similar fashion.

A biofilm may be able to adapt to a variety of ecological environments. Specifically, a biofilm may contain a number of microorganisms which perform various functions such as, for example, storing nutrition in an aqueous-based system, exhibiting resilience to variations in pH, sterilization, dehydration and the like. The biofilm is able to act as a pool which allows for genetic exchange between microorganisms existing in the biofilm. The microorganisms are therefore able to exist in symbiosis. In view of the above, the biofilm is capable of behaving like a microorganism group which may exhibit an ecological niche relating to, for example, the decomposition of various materials.

With respect to microelectronic device fabrication, the residence time of water passing through a flow line is usually shorter than the proliferation time for a microorganism, which is approximately 2 hours in a nutrient-empty environment. Thus, the proliferation of the microorganism inside ultrapure or deionized water may not impact microelectronic device production quality control. Therefore, quality control may be most greatly influenced by the ultrapure water delivery system, the line of production, or the biofilm grown on the surface of raw materials employed in a microelectronic device fabrication process.

It has been observed that a biofilm is capable of existing in ultrapure water having a resistivity of 180 M$\Omega$·cm. This is potentially significant since ultrapure water having the above resistivity is often used in fabricating highly-integrated microelectronic devices. It has been found that between $10^7$ and $10^{11}$ microorganism cells per milliliter may be present in a biofilm even when the concentration of microorganisms inside the water ranges from 1 to 10 colony forming units (cfu) per milliliter.

Microorganisms which may exist in a biofilm are capable of slowly migrating from the biofilm into the surrounding ultrapure water. These materials may thus serve as a potential contamination source. Therefore, it may be desirable to remove both the biofilm existing in an ultrapure water delivery system and ultrapure water line as well as microorganisms which may be present in the water.

Attempts at removing the microorganisms have generally involved employing biocide to physiologically deactivate the microorganisms. Nonetheless, the deactivated microorganism may still be able to attach to a material surface and serve as a surface for a newly-introduced microorganism to adhere. Moreover, the presence of a single microorganism floating on a biofilm may be troublesome since it is typically difficult to sterilize the single microorganism because it often forms a matrix structure with other microorganisms or the EPS produced thereby.

The amount of formed biofilm and microorganisms associated with the biofilm is often influenced by elements such as types and amounts of available nutrients, water shear forces, and the like, irrespective of the amount of microorganisms present in the water itself. Therefore, it may be of greater importance to remove the microconsortia-containing biofilm relative to sterilization of the microorganism itself. Removal of the biofilm, however, has often been difficult. A conventional removal technique has focused on employing a two-step process. The first step typically involves reducing the attraction between the substance surface or biofilm matrix by applying oxidizing agents, biodipersants, surfactants, enzymes, or a combination thereof. It is intended in the first step that the chemicals not affect the microorganism to eventually be treated. The second step typically involves removing the microorganism deposit, including the biofilm, from the substance surface using a physical technique involving the application of a shear force, ultrasonic energy, and the like.

A chemical sterilizer which may be used in removing a microorganism-forming biofilm should satisfy the following conditions. First, the sterilization should remove the microorganism as completely as possible. Incomplete microorganism removal may result in the re-proliferation of microorganisms. Second, the sterilizer itself should be removed subsequent to use. In particular, in the event that the sterilizer removal is incomplete, the residual may serve as a contaminant. It is also desirable to remove the sterilizer from an economic standpoint. Typically, the sterilizer is removed by cleaning the equipment or pipeline by using sterilizer-treated ultrapure water. Preferably, an on-line measurement of the density of the sterilizer should be made in conjunction with the above. Third, the sterilizer should not damage the fabrication system components either physically or chemically. Fourth, it is desirable that the sterilizer be relatively safe and easy to handle.

Hydrogen peroxide has been used as a sterilizer in an attempt to satisfy the above criteria. Conventional methods of sterilizing an ultrapure water delivery system using hydrogen peroxide have been employed in Samsung Semiconductor Manufacturing Facilities and Mitsubishi Semiconductor of America Facilities. The use of hydrogen peroxide may be advantageous in that little residue may remain on the equipment after sterilization. Moreover, pipeline corrosion may not be experienced since the hydrogen peroxide decomposes to water and oxygen after the sterilization is carried out.

It has been observed that the sterilization may be effective when the hydrogen peroxide is present in high concentrations at high temperatures. Nonetheless, if the temperatures are excessive, the pipeline used to transport the hydrogen peroxide may become damaged. Thus, there is an increased possibility that an organic or inorganic substance may be discharged from the pipeline. In view of such, it may be desirable to carry out the sterilization at a temperature of about 25° C. In addition, it may be desirable to employ a lower concentration of hydrogen peroxide since a high concentration level may result in increased solution expense and increased sterilizer removal time. Additionally, at higher hydrogen peroxide concentration levels, the reaction of a microorganism and the hydrogen peroxide may result in undesirable gas generation. In light of the above, hydrogen peroxide having a concentration of 1 weight percent is typically used in a sterilization procedure.

A sterilization technique using hydrogen peroxide as described above is often employed in the semiconductor manufacturing facilities. However, with respect to microorganism sterilization in pipelines, complete microorganism removal may not be accomplished by the use of hydrogen peroxide. More specifically, sterilization with hydrogen peroxide may only provide a temporary effect, and thus the microorganism may reproliferate. In addition, using hydrogen peroxide in a pipeline may be difficult in that individual pipelines often tend to have different sterilization requirements.

FIG. 1 shows a conventional ultrapure water delivery system and Table 1 sets forth the results of a corresponding sterilization as measured by an Acridine Orange Direct Count (AODC) technique. In this instance, the AODC technique involved first dying the microorganism colony using acridine orange dyestuff, and then counting the number of colonies using an optical microscope. As shown in Table 1, complete sterilization is not realized using only hydrogen peroxide. At an early stage of the process, sterilization is achieved at a given level. Within three months after sterilization however, the number of microorganisms increases as shown in Table 1.

TABLE 1

Number of Microorganisms Present in Various Sections of an Ultrapure Delivery System

|  |  | Before cleaning by $H_2O_2$ (cfu) | after cleaning by $H_2O_2$ (cfu) | remaining percentage | Remaining Percentage After one month | Remaining Percentage After two months | Remaining percentage after three months |
|---|---|---|---|---|---|---|---|
| filter | A | 143 | 14 | 9.8 | 29 | 58 | 158 |
| inlet | B | 141 | 28 | 19.8 | 38 | 83 | 182 |
| filter | C | 121 | 1.81 | 1.5 | 45 | 98 | 147 |
| outlet | D | 161 | 4.68 | 2.9 | 32 | 82 | 180 |
| wet- | E | 398 | 9.84 | 2.4 | 89 | 287 | 428 |
| bath | F | 239 | 60.35 | 25 | 127 | 179 | 304 |
|  | G | 709 | 25.03 | 3.5 | 74 | 389 | 655 |

A, B, C, D, E, F, G, are used for distinction of measuring sites.

Numerous difficulties may exist with respect to conventional sterilization techniques. Since an ultrapure pipeline may require a longer sterilization cycle than does an ultrapure water delivery system, is often required to increase the cleaning frequency for the ultrapure pipeline. Also, it is often difficult to remove biofilm-forming matrices. The sterilization and removal of bacteria from the inside of a polisher (which typically includes an ion-exchange resin) is also typically troublesome and is believed to be attributable to the chemical characteristics of the ion-exchange resin. Furthermore, it is typically difficult to sterilize microorganisms contained within the biofilm since biofilms often tend to form prophylactic layers which are typically difficult to penetrate A single application of hydrogen peroxide as a sterilizer may therefore be ineffective at microorganism removal. Accordingly, repeated applications of hydrogen peroxide are often necessary.

There exists a need in the art for compositions useful for sterilizing water employed in manufacturing microelectronic devices which are potentially able to yield ultrapure water in an efficient manner, along with methods of using the same.

SUMMARY OF THE INVENTION

It is an object of the present invention to provide compositions useful for sterilizing water and methods of using the same which may remove biofilms from ultrapure water delivery systems.

It is another object of the present invention to provide compositions useful for sterilizing water and methods of using the same which are capable of yielding ultrapure water without the necessity of repeated applications of chemicals.

These and other objects and advantages are provided by the present invention. In one aspect, the invention provides compositions useful for sterilizing water used in microelectronic device fabrication processes. The compositions comprise hydrogen peroxide, peracetic acid, and water. Preferably, the compositions are employed at room temperature.

In another aspect, the invention relates to methods of sterilizing ultrapure water delivery systems for use in microelectronic device fabrication processes. The methods comprise contacting the ultrapure water delivery systems with water having temperatures ranging from about 26° C. to about 40° C. The ultrapure water delivery systems are then sterilized with compositions comprising hydrogen peroxide, peracetic acid, and water.

In yet another aspect, the invention relates to ultrapure water delivery systems. The systems comprise water tanks; first heat exchangers in fluid communication with the water tanks; ultraviolet sterilizers in fluid communication with the heat exchangers; OR-polishers in fluid communication with the ultraviolet sterilizers; MB-polishers in fluid communication with the OR-polishers; ultrafilters in fluid communication with the MB-polishers; by-pass lines in fluid communication with the ultraviolet sterilizers and the ultrafilters, wherein the by-pass lines by-pass the OR-polishers and the MB-polishers; and second heat exchangers in fluid communication with the OR-polishers and the MB-polishers.

DETAILED DESCRIPTION OF THE PREFERRED EMBODIMENTS

Figure 1:
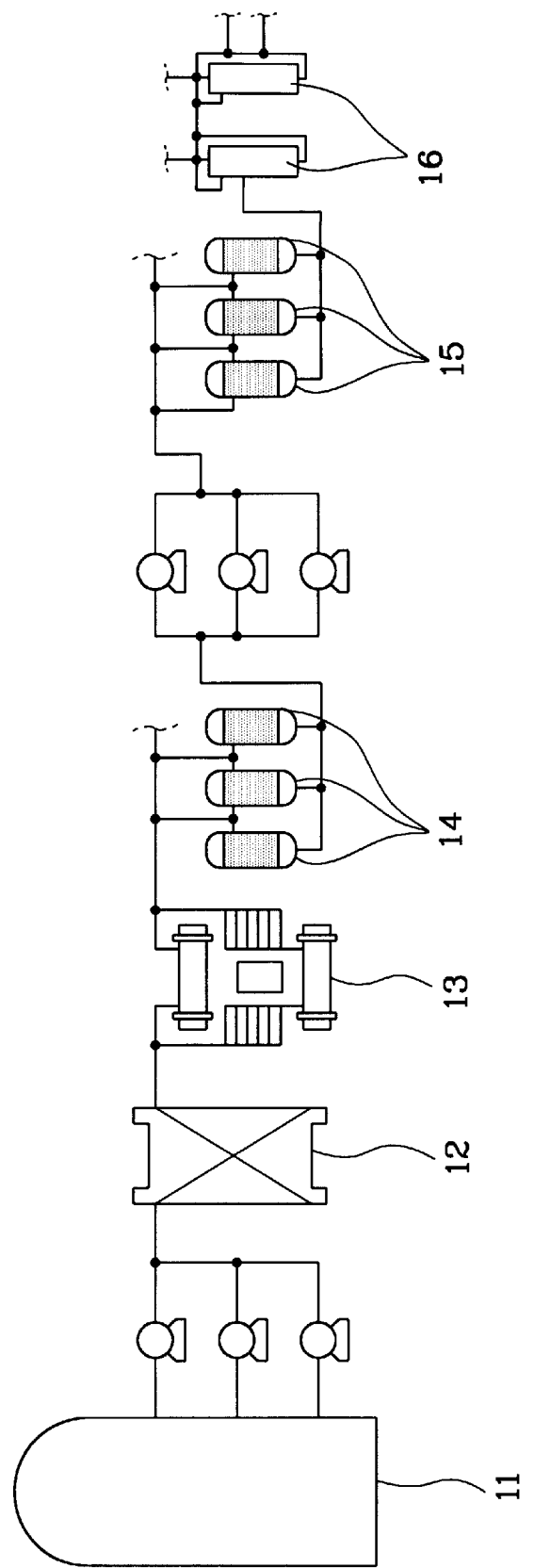
FIG. 1 illustrates a conventional ultrapure water delivery system.

The present invention now will be described more fully hereinafter with reference to the accompanying drawings and examples, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

In one aspect, the invention relates to compositions for sterilizing water used in microelectronic device fabrication processes. Preferably, the sterilized water is ultrapure water. For the purposes of the invention, the term "ultrapure water" refers to water having zero colony forming units (cfu) of microorganisms present therein. The compositions comprise hydrogen peroxide, peracetic acid, and water. Preferably, deionized water is employed in the compositions. Preferably, the compositions are employed at room temperature.

Hydrogen peroxide is believed to be desirable since it generally possesses good oxidizing and sterilization abilities which may be attributable to the presence of nascent oxygen formed upon decomposition of the compound. The hydrogen peroxide has been observed to oxidize organic material, and thus may be able to remove biofilms formed on the ultrapure water delivery systems and delivery lines connected thereto. The hydrogen peroxide may also be able to sterilize microorganisms, retard the activity of the microorganisms, and inhibit the proliferation of these materials. Furthermore, hydrogen peroxide typically does not contain metallic ions and thus may be easily cleaned. Accordingly, the use of hydrogen peroxide may reduce the potential for equipment recontamination since water and oxygen are typically produced as by-products upon decomposition of the material.

Peracetic acid which is used in the compositions of the invention may be formed according to known techniques. For example, the compound may be formed by adding hydrogen peroxide and sulfur to anhydrous acetic acid, or by radiating ultraviolet rays to a mixture containing acetaldehyde, oxygen, and acetic cobalt. Peracetic acid is capable of functioning as an effective sterilizer. In particular, acetic acid, which is one of the by-products of peracetic acid, may be able to remove sodium carbonate. This is potentially significant since sodium carbonate has been observed to surround and protect biofilms.

The components of the compositions may be present in various amounts. Preferably, the compositions comprise from about 0.3 to about 0.7 weight percent of hydrogen peroxide and from about 0.03 to about 0.07 weight percent of peracetic acid. More preferably, the compositions comprise about 0.5 weight percent of hydrogen peroxide and about 0.05 weight percent of peracetic acid.

The invention will now be described in greater detail with respect to the accompanying drawings. The compositions of the invention may be used to sterilize a conventional ultrapure water delivery system illustrated in FIG. 1. The ultrapure water delivery system is one which may be used in a microelectronic device fabrication process. The ultrapure water delivery system comprises a pure water tank 11, a heat exchanger 12 in fluid communication with the water tank 11, an ultraviolet (UV)-sterilizer 13 in fluid communication with the heat exchanger 12, an OR ("Organic Material")-polisher 14 in fluid communication with the UV-sterilizer 13, an MB ("Mixed Bed")-polisher 15 in fluid communication with the OR-polisher 14, and an ultrafilter 16 in fluid communication with the MB-polisher 15. In particular, the method of the invention may be carried out by first contacting the various components of the ultrapure water delivery system with water, preferably deionized, at a temperature ranging from about 26° C. to about 40° C., more preferably about 28° C. to about 34° C. If the water has a temperature of less than about 26° C., it may not be able to satisfactorily treat the sterilizers and materials. When the water is in excess of 34° C., there is a potential that the pipes connecting the ultrapure water delivery system and the ultrapure water line may be weakened. Additionally, there is a possibility that ion-exchange resins contained in the stabilizers may be rendered inert by the excessively hot water. Thereafter, the ultrapure water delivery system is sterilized with a composition comprising hydrogen peroxide, peracetic acid, and water, preferably, deionized water. Preferably, the time for the method to take place is greater than about 60 min, and more preferably the method takes place from about 60 min. to about 120 min.

Figure 2:
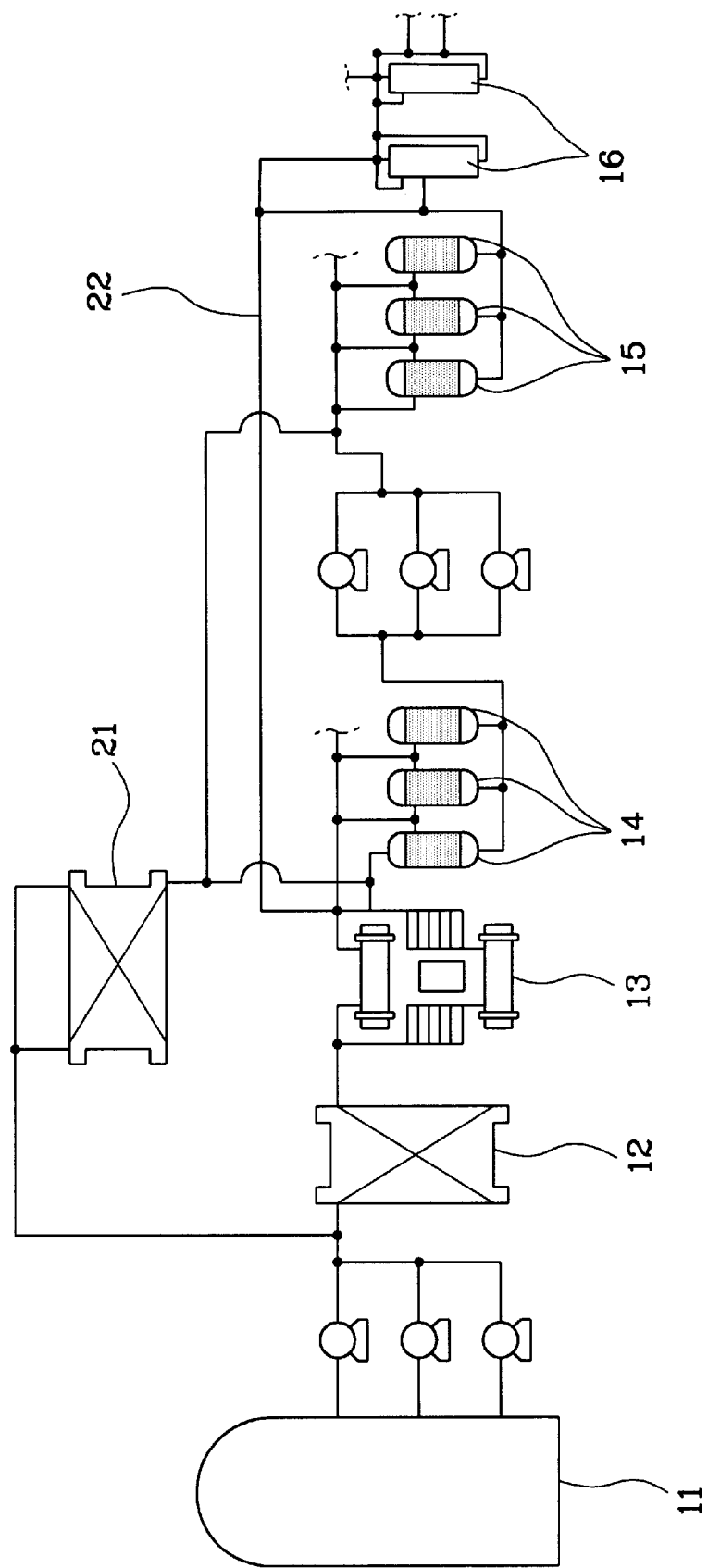
FIG. 2 illustrates an ultrapure water delivery system in accordance with the invention.
Figure 3:
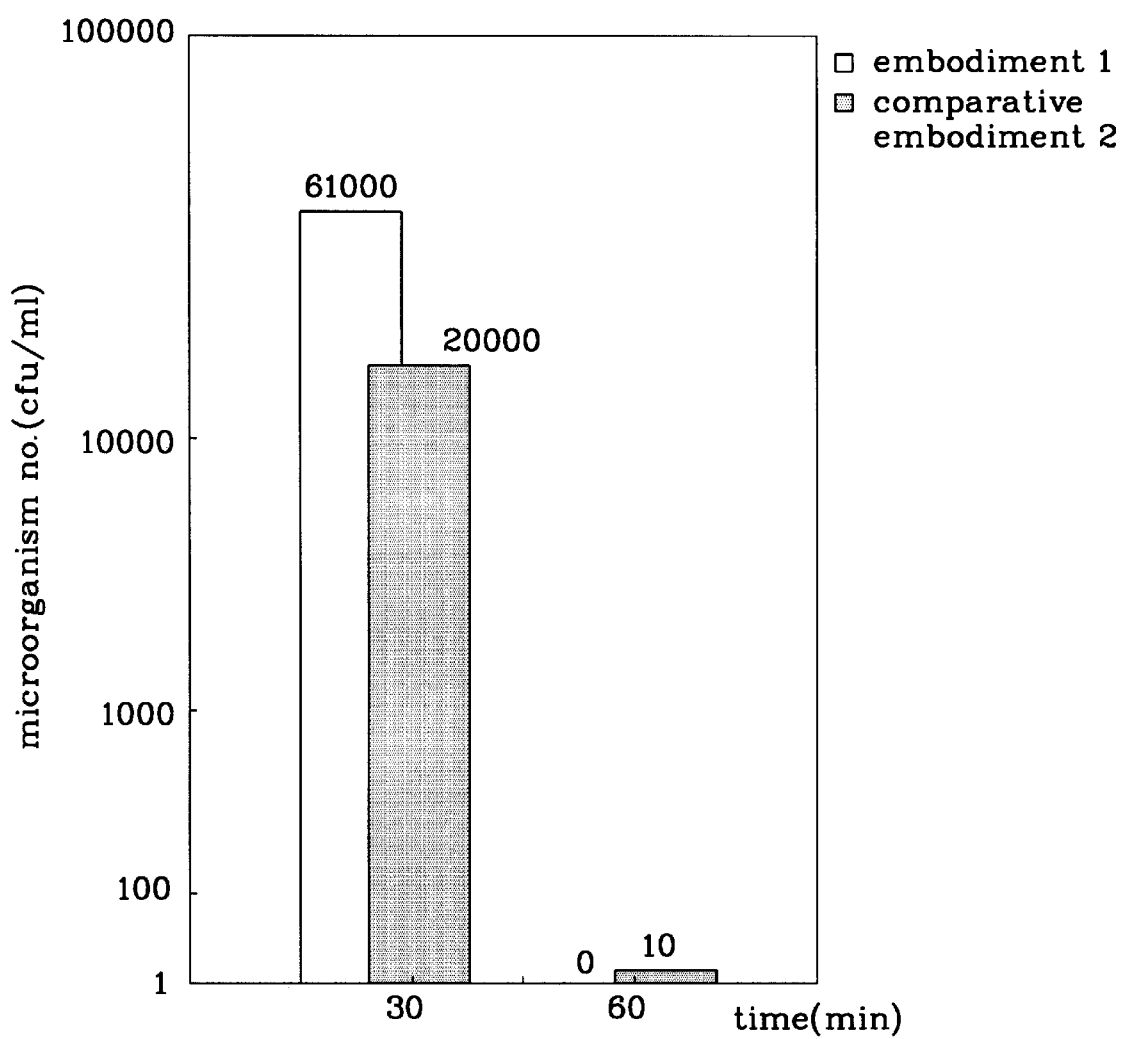
FIG. 3 is a graph comparing the results of a prior art sterilization to a sterilization of the invention.

Referring now to FIG. 2, an ultrapure water delivery system used in conjunction with a microelectronic device fabrication facility is shown. A method of sterilizing the ultrapure water delivery system comprises contacting the system with water having a temperature ranging from about 26° C. to about 40° C., more preferably about 28° C. to about 34° C. The ultrapure water delivery system is then sterilized with a composition comprising hydrogen peroxide, peracetic acid, and water. The ultrapure water delivery system comprises a pure water tank 11, a first heat exchanger 12 in fluid communication with the water tank 11, a UV-sterilizer 13 in fluid communication with the first heat exchanger 12, an OR-polisher 14 in fluid communication with the UV-sterilizer 13, an MB-polisher 15 in fluid communication with the OR-polisher 14, and an ultrafilter 16 in fluid communication with the MB-polisher 15. A second heat exchanger 21 is also present and is in fluid communication with water tank 11, the OR-polisher 14 and the MB-polisher 15. The second heat exchanger 21 is positioned to allow water to flow from water tank 11 through heat exchanger 21, and then to polishers 14 and 15. The system of the invention also includes a polisher by-pass line 22 in fluid communication with the UV-sterilizer 13 and the ultrafilter 16.

In accordance with the invention, the polisher by-pass line 22 is configured to selectively allow fluids to pass through and contact polishers 14 and 15. The by-pass line 22 may be able to allow the water at the above temperatures to pass through and contact the stabilizers 14 and 15. The by-pass line 22 also may be able to divert the compositions described herein from the polishers 14 and 15. In particular, it is believed that the hydrogen peroxide and peracetic acid components of the composition may render ion-exchange resins chemically inert if present inside the polishers 14 and 15. Thus, the composition by-passes the polishers so as to minimize loss of ion-exchange capacity. In the event that the composition contacts the ion exchange resins, the resin may have to be removed and reactivated. Alternatively, the resins may be removed and discarded and new resins can be inserted therein.

The individual components which make up the ultrapure water delivery system are known to those skilled in the art. In particular, the OR-polisher 14 may function to remove organic materials by adsorption, preferably by using an ion-exchange resin formed from organic material. The MB-polisher typically includes at least two ion exchange beds which are designed to remove inorganic materials such as metallic ions. The ion exchange beds are believed to function via an adsorption mechanism. The OR-polisher 14 and the MB-polisher 15 and the components contained therein are all known to one who is skilled in the art. Advantageously, the water which contacts the sterilizers 14 and 15, and more specifically the ion exchange resins contained therein, is able to render microorganisms and biofilm which may be attached to the resins thermally inert.

In FIGS. 1 and 2, water lines may be used for introducing water into the ultrapure water delivery systems. In particular, the water lines and the ultrapure water delivery systems may be sterilized by opening valves (not shown) which connect the water lines and the ultrapure water delivery systems. For example, a water line may be connected to ultrafilter 16.

The invention will now be described in greater detail with reference to the examples which follow. It should be understood that the examples are set forth only to illustrate the invention, and are not meant as a limitation thereof.

EXAMPLE 1

A polisher which contains an ion exchange resin in an ultrapure water delivery system is contacted with water having a temperature of 30° C. for 30 minutes. Subsequently, the other components of the ultrapure water delivery system are sterilized for 60 minutes using a composition comprising 0.5 weight percent of hydrogen peroxide, 0.05 weight percent of peracetic acid, and deionized water.

Table 2 show the amounts of microorganisms which are present at the time sterilization is initiated, 30 minutes after sterilization begins, and 60 minutes after sterilization begins. The microorganisms which are sterilized belong to the genus *Micrococcus luteus* and Pseudomonas. The microorganisms which are present before and after sterilization are retrieved in water samples and the resulting colonies are dyed using an Acridine Orange Direct Count (AODC) method. The number of colonies were determined using an optical microscope, and are expressed in Table 2 as colony forming units (cfu).

EXAMPLE 2

An ultrapure water delivery system similar to that described in Example 1 is sterilized using a composition comprising 0.5 weight percent of hydrogen peroxide, 0.1 weight percent of peracetic acid, and deionized water. The results are set forth in Table 2.

EXAMPLE 3

An ultrapure water delivery system similar to that described in Example 1 is sterilized using a composition comprising 1.0 weight percent of hydrogen peroxide, 0.05 weight percent of hydrogen peroxide, and deionized water. The results are set forth in Table 2.

EXAMPLE 4

An ultrapure water delivery system similar to that described in Example 1 is sterilized using a composition comprising 1.0 weight percent of hydrogen peroxide, 0.1 weight percent of peracetic acid, and deionized water. The results are set forth in Table 2.

EXAMPLE 5—COMPARATIVE EXAMPLE

A conventional sterilization composition is used in conjunction with an ultrapure water delivery system similar to that described in Example 1. The sterilization composition comprises 0.5 weight percent hydrogen peroxide and deionized water. The results are set forth in Table 2.

EXAMPLE 6—COMPARATIVE EXAMPLE

A conventional sterilization composition is used in conjunction with an ultrapure water delivery system similar to that described in Example 1. The sterilization composition comprises 1.0 weight percent hydrogen peroxide and deionized water. The results are set forth in Table 2.

TABLE 2

Amounts of Microorganisms Present in Water Samples from Ultrapure Delivery Systems (cfu)

|  |  | Example 1 | Example 2 | Example 3 | Example 4 | Example 5 | Example 6 |
|---|---|---|---|---|---|---|---|
| Time (min) | 0 | $9.2 \times 10^7$ | $9.2 \times 10^7$ | $9.2 \times 10^7$ | $9.2 \times 10^7$ | $9.2 \times 10^7$ | $9.2 \times 10^7$ |
|  | 30 | $6.1 \times 10^4$ | $3.6 \times 10^3$ | $5.0 \times 10^3$ | $2.0 \times 10^3$ | $1.1 \times 10^5$ | $2.0 \times 10^4$ |
|  | 60 | 0 | 0 | 0 | 0 | $9.6 \times 10^3$ | $1.0 \times 10^1$ |

As seen from Table 2, the compositions of the invention are able to provide improved sterilization results relative to conventional compositions. It is believed that these microorganisms may possess a certain level of resistance to conventional sterilization compositions containing only hydrogen peroxide and water, as potentially recognized in Korean Patent Application No. 97-5704, entitled "New Microorganisms Having a Resistance Against Hydrogen Peroxide". Table 2 indicates that an ultrapure water delivery system may be completely sterilized using the compositions of the invention in a period of 60 minutes. Additionally, the sterilization effect realized by using the compositions of the invention may be experienced for at least six months, and potentially up to 10 months after sterilization. This is advantageous in that conventional sterilization compositions have been observed to provide a sterilization effect which may last only up to three months.

In the drawings, examples, and specification, there have been disclosed typical preferred embodiments of the invention and, although specific terms are employed, they are used in a generic and descriptive sense only and not for purposes of limitation, the scope of the invention being set forth in the following claims.

That which is claimed:

1. A method of sterilizing an ultrapure water delivery system for use in a microelectronic device, said method comprising:

contacting an ultrapure water delivery system with water having a temperature ranging from about 28° C. to about 34° C. wherein the ultrapure water delivery system consists essentially of a water tank, a heat exchanger in fluid communication with the water tank, an ultraviolet sterilizer in fluid communication with and located downstream from the heat exchanger, an OR-polisher in fluid communication with and located downstream from the heat exchanger, an OR-polisher in fluid communication with and located downstream from the ultraviolet sterilizer, an MB-polisher in fluid communication with the OR-polisher and located downstream from the ultraviolet sterilizer, and an ultrafilter in fluid communication with the OR-polisher; and sterilizing the ultrapure water delivery system with a composition comprising hydrogen peroxide, peracetic acid, and water.

2. A method according to claim 1, wherein said method takes place for greater than about 60 min.

3. A method according to claim 1, wherein said sterilization step takes place from about 60 min. to about 120 min.

4. A method according to claim 1, wherein the composition comprises from about 0.3 to about 0.7 weight percent of hydrogen peroxide, and from about 0.03 to about 0.07 weight percent of peracetic acid.

5. A method according to claim 1, wherein the composition comprises about 0.5 weight percent of hydrogen peroxide and about 0.05 weight percent of peracetic acid.

6. A method of sterilizing an ultrapure water delivery system for use in a microelectronic device, said method comprising:

contacting an ultrapure water delivery system with water having a temperature ranging from about 28° C. to about 34° C. wherein the ultrapure water delivery system consists essentially of a water tank, a heat exchanger in fluid communication with the water tank, an ultraviolet sterilizer in fluid communication with and located downstream from the heat exchanger, an OR-polisher in fluid communication with and located downstream from the ultraviolet sterilizer, an MB-polisher in fluid communication with the OR-polisher and located downstream from the ultraviolet sterilizer, an ultrafilter in fluid communication with the OR-polisher, a by-pass line in fluid communication with the UV-sterilizer and the ultrafilter wherein the by-pass line by-passes the OR-polisher and the MB-polisher; and a second heat exchanger in fluid communication with the OR-polisher, the water tank, and the MB-polisher; and sterilizing the ultrapure water delivery system with a composition comprising hydrogen peroxide, peracetic acid, and water, wherein the composition by-passes the OR-polisher and the MB-polisher.

7. A method according to claim 6, wherein said method step takes place for greater than about 60 min.

8. A method according to claim 6, wherein said method takes place from about 60 min. to about 120 min.

9. A method according to claim 6, wherein the composition comprises from about 0.3 to about 0.7 weight percent of hydrogen peroxide, and from about 0.03 to about 0.07 weight percent of peracetic acid.

10. A method according to claim 6, wherein the composition comprises about 0.5 weight percent of hydrogen peroxide and about 0.05 weight percent of peracetic acid.

* * * * *